United States Patent
Hennigan (10) Patent No.: US 10,550,059 B2
(45) Date of Patent: Feb. 4, 2020

(54) PROCESS FOR THE PRODUCTION OF ACETIC ACID

(71) Applicant: BP Chemicals Limited, Middlesex (GB)

(72) Inventor: Sean Anthony Hennigan, Hull (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 16/308,332

(22) PCT Filed: Jun. 8, 2017

(86) PCT No.: PCT/EP2017/063925
§ 371 (c)(1),
(2) Date: Dec. 7, 2018

(87) PCT Pub. No.: WO2017/216024
PCT Pub. Date: Dec. 21, 2017

(65) Prior Publication Data
US 2019/0210952 A1    Jul. 11, 2019

(30) Foreign Application Priority Data
Jun. 14, 2016   (GB) .................................. 1610338.4

(51) Int. Cl.
C07C 51/12    (2006.01)
C07C 51/44    (2006.01)
C07C 53/08    (2006.01)

(52) U.S. Cl.
CPC ............... *C07C 51/12* (2013.01); *C07C 51/44* (2013.01); *C07C 53/08* (2013.01)

(58) Field of Classification Search
CPC .......... C07C 51/12; C07C 51/44; C07C 53/08
See application file for complete search history.

(56) References Cited

U.S. PATENT DOCUMENTS

| | | | | |
|---|---|---|---|---|
| 5,932,764 A | * | 8/1999 | Morris | C07C 51/12 562/519 |
| 2010/0324333 A1 | * | 12/2010 | Breeden | C07C 51/12 562/519 |

FOREIGN PATENT DOCUMENTS

| | | |
|---|---|---|
| EP | 0846674 | 6/1998 |
| WO | 03/097567 | 11/2003 |
| WO | 2009/103948 | 8/2009 |

* cited by examiner

*Primary Examiner* — Sikarl A Witherspoon
(74) *Attorney, Agent, or Firm* — McDonnell Boehnen Hulbert & Berghoff LLP (57) ABSTRACT

A process for the production of acetic acid which process comprises the steps of. (a) introducing methanol and/or a reactive derivative thereof and carbon monoxide into a first reaction zone containing a liquid reaction composition comprising a carbonylation catalyst, optionally a carbonylation catalyst promoter, methyl iodide, methyl acetate, acetic acid and water, (b) withdrawing at least a portion of the liquid reaction composition from the first reaction zone; (c) passing at least a portion of the withdrawn liquid reaction composition to a second reaction zone, wherein a gas feed comprising carbon monoxide is added to the liquid reaction composition withdrawn from the first reaction zone at one or more points upstream of the second reaction zone, one or more points within the second reaction zone, or a combination of one or more points upstream of the second reaction zone and one or more points within the second reaction zone; and (d) passing at least a portion of the liquid reaction composition from the second reaction zone into a flash separation zone to form: a vapour fraction, which comprises acetic acid, methyl iodide, methyl acetate and low pressure off-gas; and, a liquid fraction, which comprises carbonylation catalyst and optional carbonylation catalyst promoter; wherein the flow rate in kg of gas feed comprising carbon monoxide which is added to the second reaction zone per tonne of liquid reaction composition being passed to the flash separation zone (kg/te), is in the range of from $0.5F_G$ to $1.2F_G$, wherein $F_G$ is defined according to equation 1: (1) $F_G=(0.296086962 \times t_r)+(0.369636 \times R_R)+(0.295878701 \times G_P^{0.8134})-23.3448$ wherein, $t_r$ is the residence time (seconds) of the liquid reaction composition within the second reaction zone which is calculated using equation 2: (2) $t_r=V_2/F_f$ wherein, $V_2$ is the volume of the second reaction zone (m³) and $F_f$ is the volumetric flow rate of liquid reaction composition to the flash separation zone (m³/s), $R_R$ is the reaction rate of the liquid reaction composition passed to the second reaction zone at the temperature at which it is withdrawn from the first reaction zone (mol/litre/hour), and $G_p$ is the purity of the gas feed comprising carbon monoxide which is added to the second reaction zone expressed as the mass fraction of carbon monoxide in the gas feed.

15 Claims, 2 Drawing Sheets

PROCESS FOR THE PRODUCTION OF ACETIC ACID

FIELD

The present invention relates to a process for the production of acetic acid by carbonylation of methanol and/or reactive derivative thereof.

TECHNICAL BACKGROUND

The production of acetic acid by carbonylation of methanol and/or a reactive derivative thereof in the presence of a rhodium catalyst is described in, for example, GB 1,233, 121, EP 0384652, and EP 0391680. The process in the presence of an iridium catalyst is described in, for example, GB 1,234,641, U.S. Pat. No. 3,772,380, EP 0616997, EP 0618184, EP 0786447, EP 0643034, EP 0752406.

Howard et al in Catalysis Today, 18 (1993), 325-354 describe the general rhodium and iridium-catalysed carbonylation of methanol to acetic acid. The continuous catalysed, homogeneous methanol carbonylation process is said to consist of three basic sections; reaction, purification and off-gas treatment. The reaction section comprises a stirred tank reactor, operated at elevated temperature, and a flash vessel. Liquid reaction composition is withdrawn from the reactor and is passed through a flashing valve to the flash vessel, in which a vapour fraction, comprising condensable components (including product acetic acid) and low-pressure off-gas, is separated from a liquid fraction. The vapour fraction is then passed to the purification section whilst the liquid fraction is recycled to the reactor. The purification section is said to comprise a series of distillation columns wherein impurities are removed from the acetic acid product.

EP 0685446 relates to a process for the preparation of acetic acid which comprises carbonylating methanol with carbon monoxide in a first reactor in the presence of a rhodium catalyst. The reaction fluid containing dissolved carbon monoxide is passed from the first reactor to a second reactor where the dissolved carbon monoxide, without the feeding of additional carbon monoxide, is further reacted before the reaction fluid is introduced into a flash zone.

EP 0846674 describes a liquid phase process for the production of carboxylic acid which comprises carbonylating an alkyl alcohol with carbon monoxide in a first reaction zone in the presence of an iridium catalyst wherein at least a portion of the liquid reaction composition together with dissolved and/or entrained carbon monoxide is withdrawn from the first reaction zone and is passed into a second reaction zone, and wherein at least a portion of the dissolved and/or entrained carbon monoxide in the withdrawn reaction composition is reacted by further carbonylation in the second reaction zone to produce further carboxylic acid product, prior to the reaction composition being passed into a flash zone.

WO 2009/103948 describes a process for the production of acetic acid by the carbonylation of methanol and/or a reactive derivative thereof with carbon monoxide in a reactor system comprising a first reaction zone, a second reaction zone, a flash separation zone, and one or more distillation zones to recover acetic acid product, wherein the temperature of the liquid reaction composition passed from the second reaction zone to the flash separation zone is at least 8° C. greater than the temperature of the liquid reaction composition withdrawn from the first reaction zone. The increase in temperature of the liquid reaction composition after its withdrawal from the first reaction zone prior to its passage into the flash separation zone can be achieved by the introduction of carbon monoxide into the second reaction zone, and/or the temperature increase could be achieved by applying heat to the second reaction zone.

SUMMARY

It has now been surprisingly observed that the addition of carbon monoxide to the second reaction zone may not achieve the expected increase in temperature and/or may result in an increase in the expected amount of carbon monoxide being passed to the flash separation system.

According to a first aspect of the present invention, there is provided a process for the production of acetic acid which process comprises the steps of:

(a) introducing methanol and/or a reactive derivative thereof and carbon monoxide into a first reaction zone containing a liquid reaction composition comprising a carbonylation catalyst, optionally a carbonylation catalyst promoter, methyl iodide, methyl acetate, acetic acid and water;

(b) withdrawing at least a portion of the liquid reaction composition from the first reaction zone;

(c) passing at least a portion of the withdrawn liquid reaction composition to a second reaction zone, wherein a gas feed comprising carbon monoxide is added to the liquid reaction composition withdrawn from the first reaction zone at one or more points upstream of the second reaction zone, one or more points within the second reaction zone, or a combination of one or more points upstream of the second reaction zone and one or more points within the second reaction zone; and (d) passing at least a portion of the liquid reaction composition from the second reaction zone into a flash separation zone to form a vapour fraction, which comprises acetic acid, methyl iodide, methyl acetate, and a liquid fraction, which comprises carbonylation catalyst and optional carbonylation catalyst promoter;

wherein the flow rate in kg of gas feed comprising carbon monoxide which is added to the second reaction zone per tonne of liquid reaction composition being passed to the flash separation zone (kg/te), is in the range of from $0.5F_G$ to $1.2F_G$, wherein $F_G$ is defined according to equation 1:

$$F_G = (0.296086962 \times t_r) + (0.369636 \times R_R) + (0.295878701 \times G_P^{0.8134}) - 23.3448 \quad (1)$$

wherein, $t_r$ is the residence time (seconds) of the liquid reaction composition within the second reaction zone which is calculated using equation 2:

$$t_r = V_2/F_f \quad (2)$$

wherein, $V_2$ is the volume of the second reaction zone (m³) and $F_f$ is the volumetric flow rate of liquid reaction composition to the flash separation zone (m³/s), $R_R$ is the reaction rate of the liquid reaction composition passed to the second reaction zone at the temperature at which it is withdrawn from the first reaction zone (mol/litre/hour), and $G_P$ is the purity of the gas feed comprising carbon monoxide which is added to the second reaction zone expressed as the mass fraction of carbon monoxide in the gas feed.

According to a second aspect of the present invention, there is provided a method for improving a process for the production of acetic acid which process comprising the steps of:

(a) introducing methanol and/or a reactive derivative thereof and carbon monoxide into a first reaction zone containing a liquid reaction composition comprising a carbonylation catalyst, optionally a carbonylation catalyst promoter, methyl iodide, methyl acetate, acetic acid and water;

(b) withdrawing at least a portion of the liquid reaction composition from the first reaction zone;

(c) passing at least a portion of the withdrawn liquid reaction composition to a second reaction zone, wherein a gas feed comprising carbon monoxide is added to the liquid reaction composition withdrawn from the first reaction zone at one or more points upstream of the second reaction zone, one or more points within the second reaction zone, or a combination of one or more points upstream of the second reaction zone and one or more points within the second reaction zone; and (d) passing at least a portion of the liquid reaction composition from the second reaction zone into a flash separation zone to form: a vapour fraction, which comprises acetic acid, methyl iodide, methyl acetate and low pressure off-gas; and, a liquid fraction, which comprises carbonylation catalyst and optional carbonylation catalyst promoter;

wherein the flow rate of the gas feed comprising carbon monoxide which is added to the second reaction zone is adjusted to be in the range of from $0.5F_G$ to $1.2F_G$, and wherein the flow rate in kg of gas feed comprising carbon monoxide which is added to the second reaction zone per tonne of liquid reaction composition being passed to the flash separation zone (kg/te), $F_G$, is calculated according to equation 1:

$$F_G = (0.296086962 \times t_r) + (0.369636 \times R_R) + (0.295878701 \times G_P^{0.8134}) - 23.3448 \quad (1)$$

wherein, $t_r$ is the residence time (seconds) of the liquid reaction composition within the second reaction zone calculated using equation 2:

$$t_r = V_2/F_f \quad (2)$$

wherein, $V_2$ is the volume of the second reaction zone (m³) and $F_f$ is the volumetric flow rate of liquid reaction composition to the flash separation zone (m³/s), $R_R$ is the reaction rate of the liquid reaction composition passed to the second reaction zone at the temperature at which it is withdrawn from the first reaction zone (mol/litre/hour), and $G_P$ is the purity of the gas feed comprising carbon monoxide which is added to the second reaction zone expressed as the mass fraction of carbon monoxide in the gas feed.

DETAILED DESCRIPTION

In the present invention, methanol and/or reactive derivatives thereof are introduced into the first reaction zone as liquid reactants, for example, methanol may be introduced into the first reaction zone as a reactant, one or more reactive derivatives may be introduced into the first reaction zone as a reactant, or a combination of methanol together with one or more reactive derivatives of methanol may be introduced into the first reaction zone as reactants. Suitable reactive derivatives of methanol include methyl acetate, dimethyl ether and methyl iodide. Preferably, methanol and/or methyl acetate are used as liquid reactants; in one embodiment, methanol is used as a reactant; in another embodiment, methyl acetate is used as a reactant; in yet another embodiment, a mixture of methanol and methyl acetate is used as reactants.

Methyl acetate may be formed in situ in the liquid reaction composition by the reaction of methanol and/or reactive derivative thereof with the acetic acid product or solvent. Preferably the concentration of methyl acetate in the liquid reaction composition in the first reaction zone is in the range 2 to 50 wt %, more preferably 3 to 35 wt %.

Preferably, the concentration of methyl iodide in the liquid reaction composition in the first reaction zone is in the range of 1 to 20 wt %, preferably 2 to 16 wt %.

The present invention may employ a group VIII noble metal carbonylation catalyst. Preferably, the carbonylation catalyst comprises rhodium, iridium or mixtures thereof. In one particular embodiment of the present invention, the carbonylation catalyst is iridium. In another particular embodiment of the present invention, the carbonylation catalyst is rhodium. The optional carbonylation catalyst promoter may, for example, be selected from alkali metal iodides, for example lithium iodide, alkaline earth metal iodides, aluminium group metal iodides, organic iodide salts, ruthenium, osmium, rhenium, and mixtures thereof. Where the catalyst is rhodium, the optional carbonylation catalyst promoter may preferably be selected from the alkali metal iodides, for example lithium iodide, alkaline earth metal iodides, aluminium group metal iodides and/or organic iodide salts, and mixtures thereof. Where the catalyst is iridium, the optional carbonylation catalyst promoter may preferably be selected from the group consisting of ruthenium, osmium, rhenium, and mixtures thereof.

Where the carbonylation catalyst is iridium, the iridium catalyst may comprise any iridium-containing compound which is soluble in the liquid reaction composition. The iridium catalyst may be added to the liquid reaction composition in any suitable form which dissolves in the liquid reaction composition or is convertible to a soluble form. Preferably the iridium may be used as a chloride free compound such as acetates which are soluble in one or more of the liquid reaction composition components, for example water and/or acetic acid and so may be added to the reaction as solutions therein. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^- H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3.4H_2O$, $IrBr_3.4H_2O$, $Ir_3(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $H_2[IrCl_6]$, preferably, chloride-free complexes of iridium such as acetates, oxalates and acetoacetates.

Preferably, the concentration of the iridium catalyst in the liquid reaction composition in the first and second reaction zones is independently in the range 100 to 6000 ppm by weight of iridium.

Where the carbonylation catalyst is iridium, the carbonylation catalyst promoter is preferably ruthenium. The promoter may comprise any ruthenium-containing compound which is soluble in the liquid reaction composition. The ruthenium promoter may be added to the liquid reaction composition in any suitable form which dissolves in the liquid reaction composition or is convertible to soluble form. Preferably, the ruthenium promoter compound may be used as chloride-free compounds such as acetates which are soluble in one or more of the liquid reaction composition components, for example water and/or acetic acid and so may be added to the reaction as solutions therein.

Examples of suitable ruthenium-containing compounds which may be used include ruthenium (III) chloride, ruthenium (III) chloride trihydrate, ruthenium (IV) chloride, ruthenium (III) bromide, ruthenium (III) iodide, ruthenium metal, ruthenium oxides, ruthenium (III) formate, [Ru(CO)$_3$ I$_3$]$^-$H$^+$, tetra(aceto)chlororuthenium (II, III), ruthenium (II) acetate, ruthenium (III) propionate, ruthenium(III) butyrate, ruthenium pentacarbonyl, triruthieniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium (II), tetrachlorobis(benzene)diruthenium(II), dichloro(cycloocta-1,5-diene)ruthenium (II) polymer and tris(acetylacetonate)ruthenium (III).

Preferably, the ruthenium-containing compounds are free of impurities which provide or generate in-situ ionic iodides which may inhibit the reaction, for example, alkali or alkaline earth metal or other metal salts.

Preferably, the ruthenium promoter is present in an effective amount up to the limit of its solubility in the liquid reaction composition, the liquid fraction and/or any liquid process streams recycled to the carbonylation reaction zones from the one or more distillation zones.

The ruthenium promoter is suitably present in the liquid reaction composition at a molar ratio of each ruthenium promoter:iridium in the range [0.1 to 100]:1, preferably [greater than 0.5]:1, more preferably [greater than 1]:1 and preferably [up to 20]:1 more preferably [up to 15]:1 and yet more preferably [up to 10]:1.

The concentration of ruthenium promoter in the liquid reaction composition in each of the first and second reaction zones is, independently, less than 6000 ppm. A suitable promoter concentration is 400 to 5000 ppm, such as 2000 to 4000 ppm.

Suitable rhodium carbonylation catalysts are described, for example, in EP-A-0 161 874, U.S. Pat. No. 6,211,405 and EP-A-0728727.

Where the carbonylation catalyst is rhodium, the rhodium catalyst concentration in the liquid reaction composition is preferably in the range 50 to 5000 ppm, preferably 100 to 1500 ppm by weight of rhodium.

Where rhodium is used as the catalyst, an alkali metal iodide, such as lithium iodide is preferably used as the promoter, as described, for example, in EP-A-0 161 874, U.S. Pat. No. 6,211,405 and EP-A-0728727.

Carbon monoxide is suitably present in the first reaction zone at a partial pressure of $1\times10^5$ to $7\times10^6$ Nm$^{-2}$, preferably $1\times10^5$ to $3.5\times10^6$ Nm$^{-2}$.

Water may be formed in situ in the liquid reaction composition, for example, by the esterification reaction of methanol and acetic acid product. Additionally or alternatively, water may be introduced independently to the first reaction zone together with or separately from other components of the liquid reaction composition. Where iridium is used as the carbonylation catalyst the amount of water in the liquid reaction composition in the first reaction zone is suitably at least 0.5 wt % up to maximum of 15 wt %, such as up to 10 wt %, preferably up to 8 wt %. Where rhodium is used as the carbonylation catalyst the amount of water in the first reaction zone is preferably in the range 0.1 to 15 wt %, preferably 1 to 15 wt %, more preferably 1 to 8 wt %.

The first reaction zone may comprise a conventional liquid-phase carbonylation reaction zone. The first reaction zone may be operated at a reaction pressure in the range of $1\times10^6$ to $2\times10^7$ Nm$^{-2}$, preferably $1.5\times10^6$ to $1\times10^7$ Nm$^{-2}$, more preferably $1.5\times10^6$ to $5\times10^6$ Nm$^{-2}$.

The first reaction zone may be operated at a reaction temperature in the range of from 150 to 210° C., preferably in the range of from 170 to 195° C., more preferably in the range of from 185 to 195° C.

In step b) of the present invention at least a portion of the liquid reaction composition is withdrawn from the first reaction zone, and in step c) at least a portion of the withdrawn liquid reaction composition is passed to a second reaction zone to produce additional acetic acid. Preferably, substantially all of the liquid reaction composition withdrawn from the first reaction zone is passed to the second reaction zone.

Preferably, the temperature of the liquid reaction composition withdrawn from the first reaction zone is in the range of from 150 to 210° C., preferably in the range of from 170 to 195° C., more preferably in the range of from 185 to 195° C. In one particular embodiment of the present invention, the temperature of the liquid reaction composition withdrawn from the first reaction is about the same temperature at which the first reaction zone is operated.

The second reaction zone may be operated at a reaction pressure which is substantially the same as that of the first reaction zone.

Preferably, the second reaction zone has a volume in the range of 5 to 20%, more preferably 10 to 20% of the volume of the first reaction zone.

The introduction of additional carbon monoxide into the second reaction zone typically results in an increased amount of carbonylation taking place therein. Thus, unreacted methanol present in the liquid reaction composition may be carbonylated to produce more acetic acid. Additionally, the additional carbon monoxide added may also react with methyl acetate and water present in the liquid reaction composition to form acetic acid. Such carbonylation reactions of methanol and methyl acetate are exothermic, and therefore provide a temperature increase in the second reaction zone.

Increased carbonylation in the second reaction zone itself has a number of advantages in addition to the increase in temperature. In particular, since acetic acid is produced, the vapour fraction in the flash separation zone will be even further enriched with acetic acid. Further, since methyl acetate and water may also be consumed, separation of product acetic acid from light components (which include methyl acetate and water) will require less energy than would otherwise be required.

Alternatively, since methyl acetate and water may be consumed in the second reaction zone, the first reaction zone may be operated at higher concentrations of methyl acetate and water without adversely affecting the composition of the liquid reaction composition passed into the flash separation zone; and since the formation of by-products in methanol carbonylation processes tends to decrease with increasing concentrations of methyl acetate and water, operating the first reaction zone at higher concentrations of methyl acetate and water can lead to an overall reduction in by-products.

In the present invention, the temperature of the liquid reaction composition passed from the second reaction zone to the flash separation zone is greater than the temperature of liquid reaction composition withdrawn from the first reaction zone. This increase in temperature allows improved separation of acetic acid and other condensable components from the carbonylation catalyst and optional carbonylation catalyst promoter in the flash separation zone. Thus, the vapour fraction from the flash separation zone will be richer in acetic acid, thereby allowing a higher yield of acetic acid to be achieved. Further, the volume and flow rate of the liquid fraction will be reduced.

In the present invention, at least part of the increase in temperature, preferably all of the increase in temperature, of liquid reaction composition after its withdrawal from the first reaction zone and prior to its passage into the flash separation zone is achieved by the reaction of the carbon monoxide introduced into the second reaction zone, in addition to any carbon monoxide which may be dissolved and/or entrained in the liquid reaction composition withdrawn from the first reaction zone.

Heat may optionally be applied to the second reaction zone to further increase the temperature rise of the liquid reaction composition. Thus, in one embodiment of the present invention, heat is applied to the second reaction zone.

In another embodiment of the present invention, no heat is applied to the second reaction zone and all of the increase in temperature is obtained through the increased reaction in the second reaction zone that is obtained through the addition of a gas feed comprising carbon monoxide.

It has now been surprisingly observed that the increase in temperature achieved through the addition of a gas feed comprising carbon monoxide to the second reaction zone may not correspond to the amount of carbon monoxide which has been added to the second reaction zone. In particular, it has been observed that lower temperature increases may be achieved than would have been expected based on the amount of carbon monoxide added to the second reaction zone and/or may there may be an increase in the amount of carbon monoxide being passed to the flash separation system than might have been expected based upon the amount of carbon monoxide added to the second reaction zone.

Whilst not wishing to be bound by theory, it is believed that the addition of carbon monoxide to the second reaction zone at a rate which is greater than the rate at which the carbon monoxide is consumed in the second reaction zone will result in carbon monoxide being passed through the second reaction zone unconsumed, and therefore said unconsumed carbon monoxide can not provide any increase in temperature. Moreover, the addition of amounts of the gas feed comprising carbon monoxide to the second reaction zone which exceed the ability of the liquid reaction composition flowing through the second reaction zone to solubilise the components of said gas feed within the liquid will result in the unsolubilised excess of the gas feed remaining as bubbles or slugs of gas, and thus result in an effective reduction in the volume of liquid reaction composition present in the second reaction zone. The unsolubilised gas may also be referred to as undissolved gas and the two terms may be used interchangeably. Whilst not being bound by theory, it is believed that the carbonylation reaction only occurs within the liquid phase as the catalyst is non-volatile, therefore these two effects (unconsumed carbon monoxide and unsolubilised gas) can compound with each other as the reduction in liquid volume in the second reaction zone will reduce the effective time that the liquid reaction composition is within the second reaction zone, and thus further reduce the amount of carbon monoxide that is consumed in the second reaction zone.

The use of the reaction rate for the liquid reaction composition is suitable for calculation of the carbon monoxide consumption and temperature increases in conventional large volume reactors which have relatively high residence times and where any reduction of volume of the liquid reaction composition is negligible. It has been unexpectedly found that for relatively small reactors, i.e. those which have a high gas flow and short residence time, the use of such reaction rate is no longer suitable for predicting the extent of the reaction within the reactor, as the reaction rate does not take into account losses in liquid volume due to unsolubilised gases present; therefore a modification factor would need to be applied to account for the changes in the actual liquid volume present in the reactor which are resultant from the use of high gas flow, low reactivity and high levels of unreactive components.

Thus, in order to extract the maximum benefit from the amount of carbon monoxide being added to the second reaction zone, the amount of gas feed comprising carbon monoxide added to the second reaction zone has to be carefully controlled so that the benefits achieved by the addition of carbon monoxide, such as increased concentration of acetic acid in the liquid reaction composition being passed to the flash separation zone and increase in temperature of the liquid reaction composition being passed to the flash separation zone, are not offset by the reduction in the benefits that has been observed when an excess amount of gas feed comprising carbon monoxide is added to the second reaction zone. Surprisingly, there is an optimum amount of the gas feed comprising carbon monoxide that can be added before these volume reducing effects become deleterious to the temperature rise benefit.

Thus, it has been found that the flow rate in kg of gas feed comprising carbon monoxide which is added to the second reaction zone per tonne of liquid reaction composition being passed to the flash separation zone (kg/te), should be controlled to be in the range of from $0.5F_G$ to $1.2F_G$, wherein $F_G$ is defined according to equation 1:

$$F_G = (0.296086962 \times t_r) + (0.369636 \times R_R) + (0.295878701 \times G_P^{0.8134}) - 23.3448 \quad (1)$$

Wherein:
  $t_r$ is the residence time (in seconds) of the liquid reaction composition within the second reaction zone which is calculated using equation 2:

$$t_r = V_2/F_f \quad (2)$$

Wherein in equation 2, $V_2$ is the volume of the second reaction zone (m$^3$) and $F_f$ is the volumetric flow rate of liquid reaction composition to the flash separation zone (m$^3$/s); and
  $R_R$ is the reaction rate of the liquid reaction composition passed to the second reaction zone at the temperature at which it is withdrawn from the first reaction zone (mol/litre/hour);
  $G_P$ is the purity of the gas feed comprising carbon monoxide which is added to the second reaction zone expressed as the mass fraction of carbon monoxide in the gas feed.

In a preferred embodiment of the present invention, the flow rate of the gas feed comprising carbon monoxide which is added to the second reaction zone is in the range of from $0.7F_G$ to $1.1F_G$, more preferably in the range of from $0.8F_G$ to $1.05F_G$, even more preferably in the range of from $0.9F_G$ to $1.05F_G$, and most preferably in the range of from $0.95F_G$ to $1.0F_G$.

In one particular embodiment of the present invention, the residence time of the liquid reaction composition within the second reaction zone ($t_r$) calculated using equation 2 is in the range of from 10 seconds to 5 minutes, preferably in the range of from 30 seconds to 3 minutes.

The reaction rate of the liquid reaction composition passed to the second reaction zone is determined based on the temperature at which the liquid reaction composition has been withdrawn from the first reaction zone. A skilled person would be able to determine the reaction rate for the liquid reaction composition at a given temperature through determining the kinetic relationship that relates the reaction temperature, catalyst composition and general reactor composition to the mol/l/hr reaction rate through routine experimentation, wherein such routine experimentation would be performed at a scale such that any reduction of volume of the liquid reaction composition due to unsolubilised gases is negligible and can be ignored for the purposes of determining the reaction rate, such as, for example, at pilot plant or equivalent scale.

The gas feed comprising carbon monoxide that is added to the second reaction zone may be pure or relatively pure, or it may contain varying amounts of impurities that are inert to the carbonylation reaction, for example $H_2$, $N_2$, $CO_2$ and $CH_4$.

In one particular embodiment of present invention, the gas feed comprising carbon monoxide added to the liquid reaction composition withdrawn from the first reaction zone is of the same composition as the carbon monoxide feed that is introduced into the first reaction zone.

In another particular embodiment of the present invention, the gas feed comprising carbon monoxide added to the liquid reaction composition withdrawn from the first reaction zone is a gas feed that consists essentially of carbon monoxide. In one aspect of this embodiment, the gas feed comprising carbon monoxide added to the liquid reaction composition withdrawn from the first reaction zone is a pure carbon monoxide gas feed. In another aspect of this embodiment, the gas feed comprising carbon monoxide added to the liquid reaction composition withdrawn from the first reaction zone is a carbon monoxide gas feed having a carbon monoxide purity of at least 95 vol %.

In another particular embodiment of the present invention, the gas feed comprising carbon monoxide added to the liquid reaction composition withdrawn from the first reaction zone comprises impurities. In one particular aspect of this embodiment, the gas feed comprising carbon monoxide added to the liquid reaction composition withdrawn from the first reaction zone comprises off-gas withdrawn from the first reaction zone, also known as high pressure off-gas. In another particular aspect of this embodiment, the gas feed comprising carbon monoxide added to the liquid reaction composition withdrawn from the first reaction zone consists of high pressure off-gas withdrawn from the first reaction zone.

The use of high pressure off-gas from the first reaction zone as the gas feed comprising carbon monoxide that is added to the liquid reaction composition withdrawn from the first reaction zone can advantageously allow the first reaction zone to be operated at a higher carbon monoxide partial pressure, with the resulting carbon monoxide-rich high pressure off-gas being fed to the second reaction zone. Additionally, such a configuration could eliminate the requirement for a high pressure off-gas treatment process, such as scrubbing the high pressure off-gas with a suitable solvent to recover valuable reaction components therefrom.

In certain embodiments of the present invention, the purity of the gas feed comprising carbon monoxide which is added to the second reaction zone ($G_P$) expressed as the mass fraction of carbon monoxide in the gas feed is at least 0.5 (i.e. at least 50% by mass of the gas feed is carbon monoxide), more preferably at least 0.6, even more preferably at least 0.7, most preferably at least 0.8, and is less than 1, preferably is at most 0.95, more preferably at most 0.9.

In one embodiment of the present invention, the first and second reaction zones are located in separate reaction vessels. A suitable separate reaction vessel for the second reaction zone may comprise a vessel which is capable of acting as a plug-flow reactor. The second reaction zone may, for example, be a pipe between the first reaction zone and the flash separation zone.

In an alternative embodiment of the present invention, the second reaction zone may comprise an integrated part of the reaction vessel which comprises the first reaction zone, for example, a seal pan. In a further embodiment, the second reaction zone may comprise both an integrated part of the first reaction vessel and a separate second reaction vessel. Suitably, the second reaction zone is designed so as to minimise, or substantially eliminate, back-mixing in the second reaction zone.

The gas feed comprising carbon monoxide which added to the liquid reaction composition withdrawn from the first reaction zone is introduced to such withdrawn liquid reaction composition at one or more points downstream of the first reaction zone (i.e. at a one or more points after such reaction composition has been withdrawn from the first reaction zone).

For example, the gas feed comprising carbon monoxide is added to the liquid reaction composition withdrawn from the first reaction zone at one or more points upstream of the second reaction zone, one or more points within the second reaction zone, or a combination of one or more points upstream of the second reaction zone and one or more points within the second reaction zone; that is, the gas feed comprising carbon monoxide may be added to the liquid reaction composition withdrawn from the first reaction zone at: (a) one or more points upstream of the second reaction zone, (b) one or more points within the second reaction zone, or, (c) a combination of one or more points upstream of the second reaction zone and one or more points within the second reaction zone.

In one embodiment of the present invention, the gas feed comprising carbon monoxide is added to the liquid reaction composition withdrawn from the first reaction zone at one or more points upstream of the second reaction zone. In another embodiment of the present invention, the gas feed comprising carbon monoxide is added to the liquid reaction composition withdrawn from the first reaction zone at one or more points within the second reaction zone. In yet another embodiment of the present invention, the gas feed comprising carbon monoxide is added to the liquid reaction composition withdrawn from the first reaction zone at one or more points upstream of the second reaction zone and one or more points within the second reaction zone. It would be understood by a person skilled in the art that the configuration of the second reaction zone in relation to the first reaction zone may determine the point(s) at which the gas feed comprising carbon monoxide is added to the liquid reaction composition withdrawn from the first reaction zone, for example if the liquid reaction composition is withdrawn directly from the first reaction zone into the second reaction zone, then the gas feed comprising carbon monoxide would be fed to the second reaction zone at one or more points within the second reaction zone.

In iridium catalysed, ruthenium promoted carbonylation processes it is preferred that the total amount of carbon monoxide introduced into the first reaction zone and the liquid reaction composition withdrawn from the first reaction zone is sufficient to minimise precipitation of the iridium catalyst and/or ruthenium promoter. According to EP 1506151, maintaining the concentration of carbon monoxide in the low-pressure off-gas, which can be separated from the vapour fraction formed in the flash separation zone in the one or more distillation zones, according to the formula: Y>mX+C, wherein Y is the molar concentration of carbon monoxide in the low pressure off-gas, X is the concentration in ppm by weight of ruthenium in the liquid reaction composition, m is about 0.012 and C is about −8.7, minimises precipitation of the catalyst system (that is the iridium catalyst and the ruthenium promoter). In the present invention, it is preferred that the concentration of carbon monoxide in the low-pressure off-gas is about 15 mol % greater than the value of mX+C for every 10° C. rise in the temperature of the liquid reaction composition passed into the flash separation zone compared to the temperature of the liquid reaction composition withdrawn from the first reaction zone.

In one embodiment of the present invention, methyl acetate is present in the liquid reaction composition in the second reaction zone at a concentration of up to 50 wt % based on total liquid reactor content, in a preferred embodiment, the concentration of methyl acetate in the liquid reaction composition in the second reaction zone is in the range 2 to 50 wt %, more preferably 3 to 35 wt %.

In one aspect of the present invention, the concentration of methyl acetate in the liquid reaction composition passed to the flash separation zone is at least 1.5 wt % less than the concentration of methyl acetate in the liquid reaction composition withdrawn from the first reaction zone.

The amount of water in the liquid reaction composition in the second reaction zone is typically up to about 15 wt % based on total liquid reactor content. Where iridium is used as the carbonylation catalyst the amount of water in the liquid reaction composition in the second reaction zone is preferably at least 0.5 wt % and at most 15 wt %, more preferably up to 10 wt %, for example up to 8 wt %. Where rhodium is used as the carbonylation catalyst the amount of water in the second reaction zone is preferably in the range 0.1 to 15 wt %, more preferably 1 to 15 wt %, more preferably 1 to 8 wt %.

In one aspect of the present invention, the concentration of water in the liquid reaction composition passed to the flash separation zone is at least 0.4 wt % less than the concentration of water in the liquid reaction composition withdrawn from the first reaction zone.

Preferably, the concentration of methyl iodide in the liquid reaction composition in the second reaction zone is in the range of 1 to 20 wt %, preferably 2 to 16 wt %.

In step d) of the present invention at least a portion of the liquid reaction composition from step c) is passed to the flash separation zone. Suitably, substantially all of the liquid reaction composition from step c) is passed to the flash separation zone. Additionally, one or more portions of the liquid reaction composition from step c) may be withdrawn from the second reaction zone and, for example, passed to a waste heat boiler loop or a reactor cooling loop.

The temperature of the liquid reaction composition passed to the flash separation zone in the present invention is higher than the temperature of the liquid reaction composition withdrawn from the first reaction zone.

In one particular embodiment of the present invention, the temperature of the liquid reaction composition passed to the flash separation zone is less than or equal to 215° C., preferably in the range of from 195° C. to 215° C., more preferably in the range of from 200° C. to 215° C. Maintaining the temperature of the liquid reaction composition passed to the flash separation zone at less than or equal to 215° C. may avoid certain disadvantages, such as, decomposition of the carbonylation catalyst and/or carbonylation catalyst promoter. A skilled person would be able to adjust the parameters of the present invention such that the temperature of the liquid reaction composition passed to the flash separation zone is within the desired ranges of this embodiment of the present invention, for example by controlling the flow rate of one or more of the gas feed comprising carbon monoxide or the volumetric flow rate of liquid reaction composition to the flash separation zone, or the purity of the gas feed comprising carbon monoxide.

Liquid reaction composition may be passed into the flash separation zone by means of a flashing valve.

The flash separation zone may comprise an adiabatic flash vessel. Alternatively or additionally, the flash separation zone may be heated by a heating means.

The flash separation zone may typically be operated at a pressure in the range of 0 to 10 barg, preferably 0 to 3 barg.

Preferably, at least a portion of the liquid fraction from the flash separation zone is recycled to one or both of the first reaction zone and the second reaction zone.

As described above, improved separation in the flash separation zone results in reduced volume and flow rate of the liquid fraction. Thus, where at least a portion of the liquid fraction is recycled to the first reaction zone, the reduced flow rate of the liquid fraction will result in decreased cooling in the first reaction zone. Decreased cooling in the first reaction zone may allow heat, which might otherwise be wasted, to be usefully exploited; thereby reducing the energy requirements of the process. Further, since the flow rate of the liquid fraction is reduced the flow rates of the liquid reaction composition passing from the first reaction zone to the second reaction zone and the liquid reaction composition passing from the second reaction zone to the flash separation zone will also be reduced. As a result, the amount of carbonylation catalyst and optional carbonylation catalyst promoter passed to the flash separation zone per unit of time will be reduced; and, as the vapour fraction is enriched in acetic acid, the amount of catalyst and optional promoter passed to the flash separation zone per unit of acetic acid produced will also be reduced.

Optionally, the present invention can further comprise an additional step, step e), wherein acetic acid product is recovered from the vapour fraction from the flash separation zone by one or more distillation steps in a distillation zone. The distillation zone can comprise any conventional distillation apparatus used in the production of acetic acid. For example, the distillation zone may comprise a first distillation column in which acetic acid product is separated from light components, such as methyl iodide and methyl acetate. The light components are removed overhead and may be recycled to the first or second reaction zones. Also removed overhead may be a low pressure off-gas comprising the non-condensable gases such as nitrogen, carbon monoxide, hydrogen and carbon dioxide. Such a low-pressure off-gas stream may be passed through an off-gas treatment section to remove any condensable materials such as methyl iodide, prior to being vented to atmosphere, for example, via a flare. The distillation zone may comprise further distillation columns, such as one or two further distillation columns, to remove further impurities, such as water and higher-boiling by-products, from the product acetic acid.

The temperature of the liquid reaction composition withdrawn from the first reaction zone may be measured at the outlet of the first reaction zone through which liquid reaction composition is withdrawn.

The temperature of the liquid reaction composition passed from the second reaction zone to the flash separation zone may be measured at the inlet of the flash separation zone through which liquid reaction composition is passed. Where liquid reaction composition is passed into the flash separation zone by means of a flashing valve, the temperature of the liquid reaction composition passed from the second reaction zone may be measured at the flashing valve.

The present invention may be performed as a batch or a continuous process, preferably as a continuous process.

In a second aspect of the present invention, there is provided a method for improving the process for the production of acetic acid in a methanol carbonylation reaction system comprising two reaction zones and a flash separation zone, wherein the process comprising the steps of:
(a) introducing methanol and/or a reactive derivative thereof and carbon monoxide into a first reaction zone containing a liquid reaction composition comprising a carbonylation catalyst, optionally a carbonylation catalyst promoter, methyl iodide, methyl acetate, acetic acid and water;
(b) withdrawing at least a portion of the liquid reaction composition from the first reaction zone;
(c) passing at least a portion of the withdrawn liquid reaction composition to a second reaction zone, wherein a gas feed comprising carbon monoxide is added to the liquid reaction composition withdrawn from the first reaction zone at one or more points upstream of the second reaction zone, one or more points within the second reaction zone, or a combination of one or more points upstream of the second reaction zone and one or more points within the second reaction zone; and
(d) passing at least a portion of the liquid reaction composition from the second reaction zone into a flash separation zone to form: a vapour fraction, which comprises acetic acid, methyl iodide, methyl acetate and low pressure off-gas; and, a liquid fraction, which comprises carbonylation catalyst and optional carbonylation catalyst promoter, and wherein the flow rate of the gas feed comprising carbon monoxide which is added to the second reaction zone is adjusted to be in the range of from $0.5F_G$ to $1.2F_G$.

In this second aspect of the present invention, the various embodiments as described in relation to the first aspect of the present invention are equally applicable to the method of the second aspect of the present invention.

Figure 1:
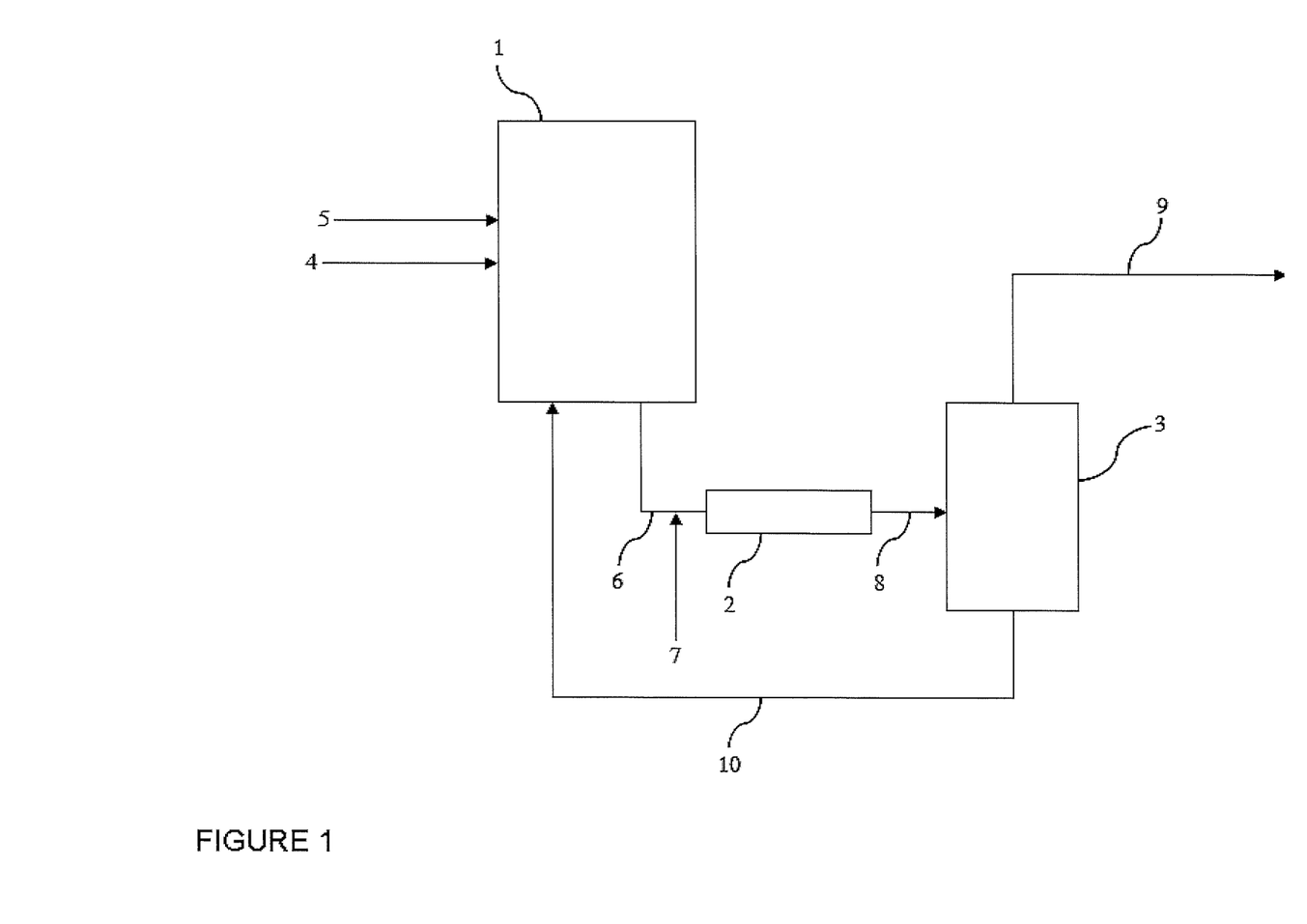
FIG. 1 is a schematic view of an apparatus in accordance with one embodiment of the present disclosure.

The present invention will now be illustrated by the following non-limiting examples and with reference to FIG. 1. FIG. 1 represents in schematic form, apparatus suitable for carrying out the present invention.

The apparatus comprises a first reaction zone (1) a second reaction zone (2), a flash separation zone (3) and a combined light ends and drying distillation column (not shown). In use, methanol and carbon monoxide are fed to the first reaction zone (1) via lines (4) and (5) respectively. In the first reaction zone (1) carbon monoxide is contacted with a liquid reaction composition which comprises the carbonylation catalyst, optional carbonylation catalyst promoter, methanol, methyl acetate, water, methyl iodide and acetic acid. Liquid reaction composition is withdrawn from the first reaction zone (1) via line (6), and is passed to the second reaction zone (2), into which an additional supply of carbon monoxide is fed via line (7). The liquid reaction composition from the second reaction zone (2) is passed to flash separation zone (3), via a flashing valve (8) wherein it is separated into two phases: a vapour fraction and a liquid fraction. The vapour fraction comprising acetic acid, methyl iodide, water, methanol and methyl acetate, is fed via line (9) to a distillation zone, comprising a combined light ends and drying column (not shown), from which low pressure off-gas is removed, for recovery of purified acetic acid. The liquid fraction, comprising catalytic species and acetic acid, is returned to the first reaction zone (1) via line (10).

In the following examples the production of acetic acid by carbonylating methanol with carbon monoxide in the presence of an iridium catalyst and ruthenium promoter, using the apparatus of FIG. 1 was simulated using an ASPEN PLUS (Trademark) (version 7.3) computer model. In the simulation, the first reaction zone (1) comprised a primary carbonylation stirred tank reactor, the second reaction zone (2) comprised a secondary plug-flow reactor, having a reduced volume compared to the primary carbonylation stirred tank reactor, the volume being such that the residence time of the secondary reaction zone (based on liquid only feed to the secondary zone) is maintained at a predetermined residence time, and the flash separation zone (3) comprised an adiabatic flash vessel. The liquid reaction composition in the primary reactor was 0.45% wt catalyst plus promoter, 5% wt water, 7% wt methyl iodide and 11% wt methyl acetate. The operating pressure of the primary reactor was $2.85 \times 10^6$ $Nm^{-2}$, and the temperature of the primary reactor was maintained at approximately 193° C. The primary reactor was fitted with a stirrer/propeller and a baffle cage to ensure intimate mixing of the liquid and gaseous reactants. Carbon monoxide was supplied to the primary reactor via a sparge fitted beneath the stirrer. The adiabatic flash vessel was operated at a pressure of $2.38 \times 10^5$ $Nm^{-2}$. A high pressure off-gas was purged from the head of the primary reactor. The reaction rate of the liquid reaction composition passed to the second reaction zone at the temperature at which it is withdrawn from the first reaction zone was set at a fixed value in the range of from 21.15-25.85 mol/litre/hour.

Using the above-described parameters, a series of simulations were performed to ascertain the effect of gas flow rate to the second reaction zone.

The addition of carbon monoxide to the second reaction zone resulted in additional exothermic reaction occurring within the second reaction zone, consequently, the temperature at the flash separation zone increased with increasing gas flow rates up to a maximum temperature increase, after which the use of higher gas flow rates resulted in a temperature increase at the flash separation zone which was lower than the maximum temperature increase.

Figure 2:
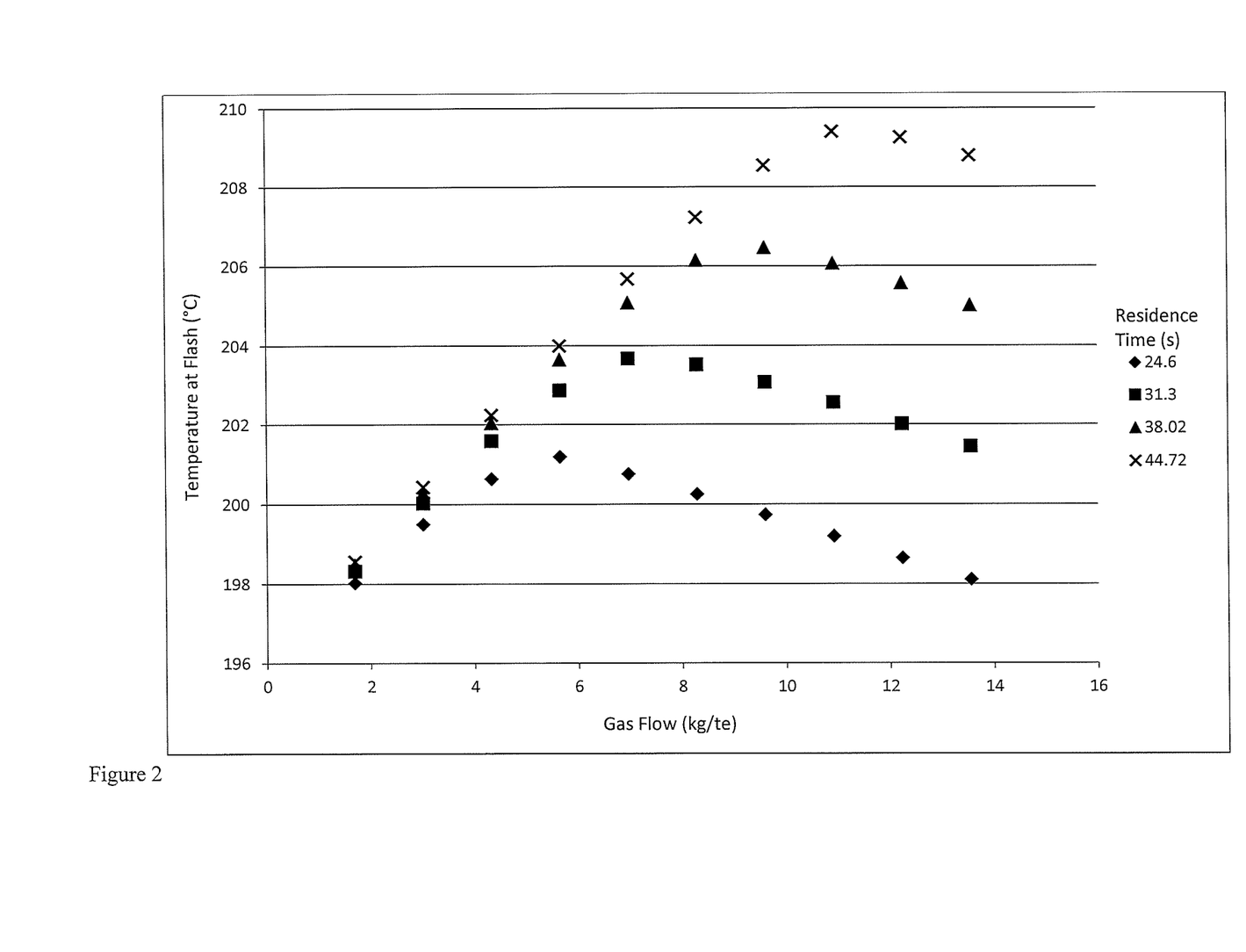
FIG. 2 is a plot showing the effect of gas flow rate on the temperature at flash for four different residence times in a system described herein.

FIG. 2 depicts the effect of gas flow rate on the temperature at the flash separation zone for four different residence times (based on liquid only feed to the second reaction zone) in a system as described above having a gas feed of pure carbon monoxide and a reaction rate of 23.5 mol/l/hr. As can be clearly seen in FIG. 2, for each of the residence times, the temperature at the flash separation zone initially increases with increasing gas flow rate up to a maximum temperature achievable for the reaction system, after which point the temperature at the flash separation zone decreases with increasing gas flow rates.

Table 1 presents the gas flow rate at which the maximum temperature increase at the flash separation zone is achieved, the 'peak gas flow', as a function of the inherent reaction rate, CO purity and residence time.

TABLE 1

| Reaction Rate (mol/l/hr) | CO Purity (mass %) | Residence time (s) | Peak Gas flow (kg/te) |
|---|---|---|---|
| 23.5 | 100 | 24.6 | 5.762711864 |
| 23.5 | 100 | 31.3 | 7.288135593 |
| 23.5 | 100 | 38.02 | 9.491525424 |
| 23.5 | 100 | 44.7 | 10.84745763 |

TABLE 1-continued

| Reaction Rate (mol/l/hr) | CO Purity (mass %) | Residence time (s) | Peak Gas flow (kg/te) |
|---|---|---|---|
| 23.5 | 80 | 24.6 | 3.38 |
| 23.5 | 80 | 31.3 | 5.423728814 |
| 23.5 | 80 | 38.02 | 7.457627119 |
| 23.5 | 80 | 44.7 | 9.491525424 |
| 23.5 | 50 | 31.3 | 1.694915254 |
| 23.5 | 50 | 38.02 | 3.389830508 |
| 23.5 | 50 | 44.7 | 4.406779661 |
| 25.85 | 100 | 24.6 | 6.101694915 |
| 25.85 | 100 | 31.3 | 8.305084746 |
| 25.85 | 100 | 38.02 | 10.50847458 |
| 25.85 | 100 | 44.7 | 12.20338983 |
| 25.85 | 80 | 31.3 | 6.440677966 |
| 25.85 | 80 | 38.02 | 8.474576271 |
| 25.85 | 80 | 44.7 | 11.18644068 |
| 25.85 | 50 | 31.3 | 3.050847458 |
| 25.85 | 50 | 38.02 | 4.406779661 |
| 25.85 | 50 | 44.7 | 5.627118644 |
| 21.15 | 100 | 24.6 | 5.050847458 |
| 21.15 | 100 | 31.3 | 6.779661017 |
| 21.15 | 100 | 38.02 | 8.13559322 |
| 21.15 | 100 | 44.7 | 9.491525424 |
| 21.15 | 80 | 24.6 | 3.01695 |
| 21.15 | 80 | 31.3 | 4.06779661 |
| 21.15 | 80 | 38.02 | 6.440677966 |
| 21.15 | 80 | 44.7 | 8.13559322 |
| 21.15 | 50 | 31.3 | 1.694915254 |
| 21.15 | 50 | 38.02 | 2.983050847 |
| 21.15 | 50 | 44.7 | 4.06779661 |

What is claimed is:

1. A process for the production of acetic acid which process comprises the steps of:
   (a) introducing methanol and/or a reactive derivative thereof and carbon monoxide into a first reaction zone containing a liquid reaction composition comprising a carbonylation catalyst, optionally a carbonylation catalyst promoter, methyl iodide, methyl acetate, acetic acid and water;
   (b) withdrawing at least a portion of the liquid reaction composition from the first reaction zone;
   (c) passing at least a portion of the withdrawn liquid reaction composition to a second reaction zone, wherein a gas feed comprising carbon monoxide is added to the liquid reaction composition withdrawn from the first reaction zone at one or more points upstream of the second reaction zone, one or more points within the second reaction zone, or a combination of one or more points upstream of the second reaction zone and one or more points within the second reaction zone; and
   (d) passing at least a portion of the liquid reaction composition from the second reaction zone into a flash separation zone to form a vapour fraction, which comprises acetic acid, methyl iodide, methyl acetate, and a liquid fraction, which comprises carbonylation catalyst and optional carbonylation catalyst promoter;
   wherein the flow rate in kg of gas feed comprising carbon monoxide which is added to the second reaction zone per tonne of liquid reaction composition being passed to the flash separation zone (kg/te), is in the range of from $0.5F_G$ to $1.2F_G$, wherein $F_G$ is defined according to equation 1:

$$F_G=(0.296086962 \times t_r)+(0.369636 \times R_R)+(0.295878701 \times G_P^{0.8134})-23.3448 \quad (1)$$

wherein, $t_r$ is the residence time (seconds) of the liquid reaction composition within the second reaction zone which is calculated using equation 2:

$$t_r=V_2/F_f \quad (2)$$

wherein, $V_2$ is the volume of the second reaction zone (m$^3$) and $F_f$ is the volumetric flow rate of liquid reaction composition to the flash separation zone (m$^3$/s), $R_R$ is the reaction rate of the liquid reaction composition passed to the second reaction zone at the temperature at which it is withdrawn from the first reaction zone (mol/litre/hour), and $G_P$ is the purity of the gas feed comprising carbon monoxide which is added to the second reaction zone expressed as the mass fraction of carbon monoxide in the gas feed.

2. A process according to claim 1, wherein the flow rate of the gas feed comprising carbon monoxide which is added to the second reaction zone is in the range of from $0.7F_G$ to $1.1F_G$.

3. A process according to claim 1, wherein the gas feed comprising carbon monoxide added to the liquid reaction composition withdrawn from the first reaction zone is of the same composition as the carbon monoxide that is introduced into the first reaction zone.

4. A process according to claim 1, wherein the gas feed comprising carbon monoxide added to the liquid reaction composition withdrawn from the first reaction zone is pure carbon monoxide.

5. A process according to claim 1, wherein the gas feed comprising carbon monoxide added to the liquid reaction composition withdrawn from the first reaction zone comprises impurities.

6. A process according to claim 5, wherein the gas feed comprising carbon monoxide added to the liquid reaction composition withdrawn from the first reaction zone comprises high pressure off-gas from the first reaction zone.

7. A process according to claim 5, wherein the gas feed comprising carbon monoxide added to the liquid reaction composition withdrawn from the first reaction zone consists of high pressure off-gas from the first reaction zone.

8. A process according to claim 5, wherein $G_P$ is at least 0.5 and is less than 1.

9. A process according to claim 1, wherein $t_r$ is in the range of from 10 seconds to 5 minutes.

10. A process according to claim 1, wherein substantially all of the liquid withdrawn from the first reaction zone is passed to the second reaction zone.

11. A process according to claim 1, wherein all of the gas feed comprising carbon monoxide is added to the liquid reaction composition withdrawn from the first reaction zone upstream of the second reaction zone.

12. A process according to claim 1, wherein all of the gas feed comprising carbon monoxide is added to the liquid reaction composition withdrawn from the first reaction zone at one or more points within the second reaction zone.

13. A process according to claim 1, wherein the first and the second reaction zones are maintained in separate reaction vessels.

14. A process according to claim 1, wherein the second reaction zone comprises a section of pipe between the first reaction zone and the flash separation zone.

15. A method for improving a process for the production of acetic acid which process comprising the steps of:
   (a) introducing methanol and/or a reactive derivative thereof and carbon monoxide into a first reaction zone containing a liquid reaction composition comprising a carbonylation catalyst, optionally a carbonylation catalyst promoter, methyl iodide, methyl acetate, acetic acid and water;
   (b) withdrawing at least a portion of the liquid reaction composition from the first reaction zone;
   (c) passing at least a portion of the withdrawn liquid reaction composition to a second reaction zone, wherein a gas feed comprising carbon monoxide is added to the liquid reaction composition withdrawn from the first reaction zone at one or more points upstream of the second reaction zone, one or more points within the second reaction zone, or a combination of one or more points upstream of the second reaction zone and one or more points within the second reaction zone; and (d) passing at least a portion of the liquid reaction composition from the second reaction zone into a flash separation zone to form: a vapour fraction, which comprises acetic acid, methyl iodide, methyl acetate and low pressure off-gas; and, a liquid fraction, which comprises carbonylation catalyst and optional carbonylation catalyst promoter;

wherein a flow rate in kg of gas feed comprising carbon monoxide which is added to the second reaction zone per tonne of liquid reaction composition being passed to the flash separation zone (kg/te), $F_G$, is calculated according to equation 1:

$$F_G = (0.296086962 \times t_r) + (0.369636 \times R_R) + (0.295878701 \times G_P^{0.8134}) - 23.3448 \qquad (1)$$

wherein, $t_r$ is the residence time (seconds) of the liquid reaction composition within the second reaction zone which is calculated using equation 2:

$$t_r = V_2/F_f \qquad (2)$$

wherein, $V_2$ is the volume of the second reaction zone (m$^3$) and $F_f$ is the volumetric flow rate of liquid reaction composition to the flash separation zone (m$^3$/s), $R_R$ is the reaction rate of the liquid reaction composition passed to the second reaction zone at the temperature at which it is withdrawn from the first reaction zone (mol/litre/hour), and $G_P$ is the purity of the gas feed comprising carbon monoxide which is added to the second reaction zone expressed as the mass fraction of carbon monoxide in the gas feed; and the flow rate of the gas feed comprising carbon monoxide which is added to the second reaction zone is adjusted to be in the range of from $0.5F_G$ to $1.2F_G$.

* * * * *